(12) United States Patent
    Schlegel et al.

(10) Patent No.: US 10,085,662 B2
(45) Date of Patent: Oct. 2, 2018

(54) DEVICE AND METHOD FOR DIGITAL-TO-ANALOG TRANSFORMATIONS AND RECONSTRUCTIONS OF MULTI-CHANNEL ELECTROCARDIOGRAMS

(71) Applicants: Todd T. Schlegel, Nassau Bay, TX (US); Walter B. Kulecz, Houston, TX (US)

(72) Inventors: Todd T. Schlegel, Nassau Bay, TX (US); Walter B. Kulecz, Houston, TX (US)

(73) Assignee: The United States of America as represented by the Administrator of the National Aeronautics and Space Administration, Washington, DC (US)

( * ) Notice: Subject to any disclaimer, the term of this patent is extended or adjusted under 35 U.S.C. 154(b) by 1233 days.

(21) Appl. No.: 13/851,778

(22) Filed: Mar. 27, 2013

(65) Prior Publication Data
    US 2014/0296722 A1    Oct. 2, 2014

Related U.S. Application Data

(60) Provisional application No. 61/720,207, filed on Oct. 30, 2012.

(51) Int. Cl.
    *A61B 5/04*    (2006.01)
    *A61B 5/0402*  (2006.01)
(52) U.S. Cl.
    CPC ........ *A61B 5/04012* (2013.01); *A61B 5/0402* (2013.01)

(58) Field of Classification Search
    CPC ... A61B 5/0402; A61B 5/7221; A61B 5/7203;
                    A61B 5/0004; A61B 5/0245;
    (Continued)

(56) References Cited

U.S. PATENT DOCUMENTS 5,226,431 A    7/1993  Bible et al.
5,511,553 A *  4/1996  Segalowitz .......... A61B 5/0006
                                                   128/903

(Continued)

OTHER PUBLICATIONS

Shah et al., ClearCorrect v. ITC: Federal Circuit Hears Argument in Case Which Will Decide Whether ITC Has Jurisdiction Over Digital Imports, Global IP Matters Mintz Levin , Aug. 2015, pp. 1-3.

(Continued)

*Primary Examiner* — Deborah Malamud
(74) *Attorney, Agent, or Firm* — Theodore U. Ro; Edward K. Fein; Mark P. Dvorscak

(57) ABSTRACT

The present invention includes a method and apparatus for digital to analog conversion and reconstruction of multi-channel electrocardiograms. The method may include receiving digital information representative of a plurality of independent signals, producing a plurality of analog outputs from said digital information wherein a first analog output is designated as a common reference, and imposing a predetermined voltage on a second analog output with respect to said common reference, which provides for a substantial recreation of the original independent signals. The apparatus may comprise a processor operable for receiving digital information representative of independent lead signals from a first ECG machine and digital to analog circuitry for substantially reproducing the original lead signals for analysis on a second ECG machine for convenient and efficient second opinions of cardiac data.

13 Claims, 8 Drawing Sheets

(58) Field of Classification Search
CPC . A61B 5/7225; A61B 5/04017; A61B 5/0006; A61B 5/04012; A61B 5/00; A61B 5/04; A61B 5/486; A61B 5/72; A61N 1/08
USPC ........................................................ 600/509
See application file for complete search history.

(56) References Cited

U.S. PATENT DOCUMENTS

| | | | |
|---|---|---|---|
| 6,183,417 B1 * | 2/2001 | Geheb | G06F 19/3406 600/301 |
| 6,360,117 B1 | 3/2002 | Kuo | |
| 6,520,910 B1 | 2/2003 | Kohls | |
| 6,611,705 B2 | 8/2003 | Hopman et al. | |
| 6,685,633 B2 | 2/2004 | Albert et al. | |
| 6,735,464 B2 | 5/2004 | Onoda et al. | |
| 7,184,921 B2 | 2/2007 | Kohls | |
| 7,197,357 B2 | 3/2007 | Istvan et al. | |
| 7,343,198 B2 | 3/2008 | Behbehani et al. | |
| 7,499,825 B2 | 3/2009 | Kohls et al. | |
| 7,783,339 B2 | 8/2010 | Lee et al. | |
| 7,801,593 B2 | 9/2010 | Behbehani et al. | |
| 7,860,557 B2 * | 12/2010 | Istvan | A61B 5/0006 600/391 |
| 8,082,027 B2 | 12/2011 | Young et al. | |
| 2002/0045836 A1 * | 4/2002 | Alkawwas | A61B 5/0006 600/509 |
| 2004/0267144 A1 | 12/2004 | Kuo et al. | |
| 2005/0165319 A1 | 7/2005 | Brodnick et al. | |
| 2005/0177052 A1 | 8/2005 | Istvan et al. | |
| 2005/0277840 A1 | 12/2005 | Whan | |
| 2007/0078354 A1 | 4/2007 | Holland | |
| 2007/0149887 A1 | 6/2007 | Hwang et al. | |
| 2008/0243012 A1 | 10/2008 | Fujihashi et al. | |
| 2009/0247835 A1 | 10/2009 | Voipio | |
| 2009/0299204 A1 | 12/2009 | Hsieh et al. | |
| 2009/0299771 A1 | 12/2009 | Hsieh et al. | |
| 2010/0017471 A1 | 1/2010 | Brown et al. | |
| 2010/0249623 A1 | 9/2010 | Makdissi | |
| 2010/0286524 A1 | 11/2010 | Daoura et al. | |

OTHER PUBLICATIONS

Kothadia et al., New System for Digital to Analog Transformation and Reconstruction of 12-Lead ECGs, PLOS One , Apr. 2013, vol. 1 , Issue 4, e61076, pp. 1-12.

* cited by examiner

DEVICE AND METHOD FOR DIGITAL-TO-ANALOG TRANSFORMATIONS AND RECONSTRUCTIONS OF MULTI-CHANNEL ELECTROCARDIOGRAMS This application claims benefit of U.S. patent application provisional application No. 61/720,207 filed Oct. 20, 2012, which is hereby incorporated by reference.

STATEMENT OF GOVERNMENT INTEREST

The invention described herein was made in the performance of work under a NASA contract and is subject to the provisions of Section 305 of the National Aeronautics and Space Act of 1958, Public Law 85-568 (72 Stat. 435; 42 U.S.C. 2457).

BACKGROUND OF THE INVENTION

Field of the Invention

The present invention relates generally to electrocardiogram systems and, in one more particular embodiment, to a specialized method and/or system for digital to analog conversion (DAC) and reconstruction of multichannel electrocardiograms (ECGs), including 12-lead ECGs, compatible with multiple ECG manufacturers.

Background

Most modern electrocardiogram (ECG) machines use built-in analog to digital converters (ADCs) to digitize patients' analog cardiac electrical signals for more efficient analysis, display, storage, printing, and sharing of data. While this common and intuitive method has heretofore been sufficient for most clinical uses, this process typically "locks in" the practicing clinician to the often opaque and sometimes proprietary digital format(s) of the specific ECG machine(s) being employed. In contradistinction, and particularly for patients with difficult-to-interpret 12-lead ECGs wherein the automated diagnosis from the "house machine" may be in question (no automated algorithm being error free), many clinicians might welcome the opportunity to occasionally obtain one or more additional opinions from other manufacturers' automated interpretive algorithms. Different algorithms for example are sometimes known to have widely varying diagnostic accuracies for common electrocardiographic conditions.

As noted above, this can be problematic because each manufacturer uses competing proprietary programs to analyze the ECG data, restricting physicians and/or technicians to a particular automatic diagnostic algorithm. These diagnostic algorithms have variances that cause each of them to be better suited in diagnosing certain diseases and/or defects better than others.

Furthermore, most ECG machines are only designed to receive analog data, not digital data. Therefore, should a second automated opinion be necessary or advised, a patient must normally be subjected to a second ECG test, because the second ECG machine cannot readily receive the digital information generated in the first ECG machine to generate a second analysis. Even though it would be highly desirable to analyze data utilizing the diagnostic programs of different ECG machine manufacturers, there is presently no ready solution for ECG data generated on Manufacturer X's machine to subsequently be analyzed by Manufacturer Y's machine for diagnosis and second opinions.

The following background prior art patents disclose various types of ECG apparatuses, methods and/or systems, but do not address the problems discussed hereinbefore:

U.S. Pat. No. 7,197,357, issued Mar. 27, 2007 to Istvan et al., discloses a cardiac monitoring system and, more particularly, a wireless electrocardiograph (ECG) system. The base station converts the digital signals back to analog electrical signals that can be read by an ECG monitor. However, this art is directed at removing the plethora of cables associated with ECG machines and not solving the problem of compatibility issues between competing ECG manufacturers.

U.S. Pat. No. 6,611,705, issued Aug. 26, 2003 to Hopman et al., discloses a method and system for wireless ECG monitoring. An electrode connector, transmitter and receiver operate with existing electrodes and ECG monitors. The electrode connector includes connectors for attaching to disposable or reusable single electrodes. The transmitter transmits the signals from the electrodes to the receiver. The receiver passes the electrode signals to the ECG monitor for processing. ECG monitors used with an electrical conductor, for example wire connections to electrodes, are connected with the receiver. A Legacy ECG monitor is available to connect with the receiver using the ECG monitor's lead-wires. The ECG monitor operates as if directly connected to the electrodes without wires running from the ECG monitor to the patient.

U.S. Pat. No. 3,810,102, issued May 7, 1974 to Parks III, et al., discloses a method and system for transmitting biomedical data to a remote station for subsequent processing. Analog electrical biomedical signals are sampled and digitized at a relatively low data rate and transmitted over a communications link of limited bandwidth to a remote station where the analog electrical biomedical signals are reconstructed from the digital data and are sampled and digitized at a substantially higher data rate for subsequent interpretation by a diagnostic computer. Alternatively, the received digital data are directly converted to a substantially higher digital data rate by means of a numerical algorithm, a form of digital interpolation.

U.S. Pat. No. 8,082,027, issued Dec. 20, 2011, to Young, et al., discloses a system and method of the present application comprising ECG acquisition device having a USB connector for connecting the device to a host device and a patient connector for connecting the device to a patient with ECG leads. The ECG acquisition device of the present system further includes a processor and storage medium, a power management and brokering module, a USB communications control module, an ECG acquisition circuit, and a patient isolation module. The ECG acquisition device auto-loads and runs ECG monitoring software onto the host device.

U.S. Pat. No. 7,783,339, issued Aug. 24, 2010, to Lee, et al., discloses a method and system for real-time digital filtering for electrophysiological and hemodynamic amplifiers. The invention replaces the analog circuits currently used for signal filtering and conditioning in such systems with digital filters that may be implemented in a software application. The method and system includes digitizing the analog signal collected from the patient prior to performing the signal filtering and conditioning. The method and system also includes removing stimulus artifacts, as well as performing sample rate conversion and scaling on the digital signal. The processed digital signals may be used, displayed, saved and converted to analog signal through digital-to-analog conversion.

U.S. Pat. No. 7,184,921, issued Feb. 27, 2007, to Kohls, discloses a technique for encoding physiological data, such as a digital ECG, as a set of high-resolution symbols. The set of high-resolution symbols may be printed on a printout of the physiological data or other suitable medium. The set of high-resolution symbols may be scanned, or otherwise acquired, and decoded to reconstruct all or a portion of the original set of physiological data.

U.S. Pat. No. 6,735,464, issued May 11, 2004, to Onoda, et al., discloses an electrocardiograph system having an electrocardiograph transmitting cardiograms produced to outside equipment, and a communication device wirelessly communicating with the electrocardiograph. The communication device accepts a subject's posture selected from multiple posture options, and transmits a specific instruction signal to the electrocardiograph upon receiving the selection. The electrocardiograph stores a cardiogram produced when the instruction signal is received from the communication device as a reference cardiogram corresponding to the selected posture discriminating it from other cardiograms.

U.S. Patent Application No. 20100017471, issued Jan. 21, 2010, to Brown, et al., discloses systems and methods for providing improved medical care. A system includes a defibrillator, a gateway device, a routing device, and a wireless modem. The system may further include hardware and/or software components located at a remote facility for receiving data and one or more server devices for decoding data from the remote facility. A method includes acquiring medical data at a first location, converting the medical data from an analog signal to a digital signal, transmitting the digital signal from the first location to a second location over the internet via a cellular network, receiving the digital signal at the second location, and converting the digital signal back to an analog signal for processing. The first location may be an EMS vehicle, and the second location may be a remote facility, such as a dispatch center or local hospital.

There exists a need for a specialized method and system for digital to analog conversion (DAC) and reconstruction of multichannel electrocardiograms (ECGs) which addresses the problems associated with the prior art described hereinbefore. The present invention has direct commercial, military, and/or medical applications. Furthermore, the present invention would be valuable not only for further review of ECG data and second opinions, but also for improving diagnostic algorithms amongst ECG manufacturers through collaboration. Consequently, those skilled in the art will appreciate the present invention that addresses the above and other problems.

SUMMARY OF THE INVENTION

One possible object of the present invention is to provide a specialized system for digital to analog conversion (DAC) and reconstruction of multichannel electrocardiograms (ECGs), including 12-lead ECGs. The word lead has multiple meanings in electrocardiography: for example, it refers to either the wire that connects an electrode to the electrocardiograph, or (more commonly) to a combination of electrodes that form a virtual line in the body along which the electrical signals are measured. Thus, the term loose lead artifact uses the former meaning, while the term 12-lead ECG uses the latter. In fact, a 12-lead electrocardiograph usually only uses 10 wires/electrodes.

Another possible object of the present invention is to provide a specialized system for digital to analog conversion (DAC) and reconstruction of multichannel electrocardiograms which can interface with multiple different ECG machines.

An additional possible object of the present invention is to provide a specialized electrocardiogram DAC and reconstruction system which provides for less expensive and/or less bulky front end ECG hardware for remote and impoverished areas.

Yet another possible object of the present invention is to provide a specialized electrocardiogram DAC and reconstruction system which provides for rapid automated second opinions of difficult to interpret 12-lead ECGs.

Yet another possible object of the present invention is to provide a specialized electrocardiogram DAC and reconstruction system which provides for improved performance of automated ECG interpretations, e.g., when ECG machines from multiple manufacturers are used in the same setting.

Yet another possible object of the present invention is to provide a specialized electrocardiogram DAC and reconstruction system which can further the clinical utility of technology that converts paper ECG printouts to digital ECG files.

These and other objects, features, and advantages of the present invention will become clear from the figures and description given hereinafter. It is understood that the objects listed above are not all inclusive and are only intended to aid in understanding the present invention, not to limit the bounds of the present invention in any way.

In accordance with the present invention, a specialized method and apparatus for digital to analog conversion and reconstruction of multichannel electrocardiograms is disclosed which may comprise steps such as, for example, receiving digital information representative of a plurality of independent signals (i) between a predetermined at least one pair of a plurality of electrodes placed on a living creature or (ii) between at least one individual electrode from said plurality of electrodes placed on a living creature and a predetermined reference comprising an electrical resultant or potential difference between two or more predetermined electrodes of said plurality of electrodes placed on a living creature. As used herein, a "living creature" comprises at least a plurality of limbs and a chest. For example, a living creature may be a human being having four limbs (i.e., two arms and two legs and a chest). As another example, a living creature may be a cow having four limbs (i.e., four legs and a chest). Many other examples exist. In addition, in an embodiment, a predetermined reference may be comprised of a predetermined two or more of said plurality of independent signals. Still further, in an embodiment, a predetermined reference may represent an average value of a predetermined two or more of said plurality of independent signals.

Other steps may comprise producing a plurality of analog outputs from the digital information wherein a first analog output is designated as a common reference, and imposing a predetermined voltage on a second analog output with respect to the common reference.

The method may further comprise utilizing the plurality of analog outputs for substantially recreating lead signals originally produced by placing the plurality of electrodes on the living creature which resulted in creation of the digital information.

Other steps of the method may include receiving the digital information in a predetermined format and converting the digital information in the predetermined format to a predetermined optimal format.

In an embodiment, the predetermined format may be based on utilizing an electric potential involving two or more electrodes (i.e., a group of electrodes) of the plurality of electrodes as a signal reference. Thus, in this embodiment, the step of converting the digital information from a predetermined format to an optimal format may comprise a step of assigning a common reference to a first analog output wherein the first analog output corresponds to a limb electrode. In an embodiment, the step of assigning may be executed in a digital to analog (DAC) device.

In another possible embodiment, a step of converting the digital information from a predetermined format to an optimal format may comprise assigning the common reference to a first analog output wherein the first analog output corresponds to a particular one electrode (i.e., a first electrode) of the plurality of electrodes. In another embodiment, the method may further comprise a step of utilizing DAC hardware (i.e., a DAC device) to perform the step of converting the digital information.

In one embodiment, the plurality of electrodes may comprise a plurality of limb electrodes and a plurality of precordial electrodes configured to produce an ECG recording. However, the invention is not limited to ECG recordings and may comprise other types of living creature electrode recording devices.

In one embodiment, the plurality of limb electrodes may comprise a right arm electrode, a left arm electrode, a right leg electrode, a left leg electrode, or any combination thereof. A second analog output discussed above may correspond to another particular one electrode (i.e., a second electrode) of the plurality of electrodes comprising a second limb of the living creature. The analog outputs generally correspond to and may be considered as corresponding electrodes.

In another embodiment of the present method, the step of imposing a predetermined voltage on the second analog output with respect to the common reference may comprise imposing a zero voltage on the second analog output. Imposing a zero voltage on the analog output may be done with software or hardware and may comprise directly connecting the second analog output to the common reference. In one embodiment, the method of directly connecting comprises connecting the second analog output to the common reference through a resistor, which is utilized for impedance matching, as might be used for impedance matching on an ECG machine into which the analog signals could be fed.

In one embodiment, the plurality of electrodes comprises a plurality of limb electrodes and a plurality of precordial electrodes configured to produce an ECG recording, and the plurality of analog outputs correspond to the plurality of limb electrodes and the plurality of precordial electrodes and the digital information is produced by a first ECG machine made by a first manufacturer, and further comprising connecting the plurality of analog outputs to a second ECG machine made by a second manufacturer.

In another embodiment, the method may comprise comparing a first analysis of the ECG recording produced by the first ECG machine to a second analysis of the ECG recording produced by the second ECG machine. The method may further comprise utilizing the plurality of analog signals to produce a plurality of analyses from different ECG machine manufacturers.

In an alternative embodiment of the present invention, an apparatus is provided for recreating lead signals that are substantially equivalent to those original signals produced by placing a plurality of electrodes on a living creature. Another definition of "lead" is an output from a pair of electrodes. A processor is operable for receiving digital information representative of independent lead signals, wherein each independent lead signal represents at least one of electrical potentials between pairs of the plurality of electrodes or electric potentials between individual electrodes of the plurality of electrodes and a reference representing signals, such as electric potentials, from at least two electrodes (i.e., a group of electrodes) of the plurality of electrodes.

Other elements may comprise digital to analog circuitry (which may or may not be incorporated in a digital to analog conversion hardware or device) with a plurality of analog outputs wherein one analog output is designated as a common reference and wherein a predetermined voltage is imposed on another of the analog outputs. The processor and digital to analog and/or other components may be discrete components, integrated components, firmware, and/or may be designed in optimal fashion as desired.

In this embodiment, the recreated substantially original lead signals comprise electrical potentials between the plurality of analog outputs.

The apparatus may further comprise a processor operable for receiving the digital information in a predetermined format and converting the digital information in the predetermined format to a predetermined optimal format. The processor is then operable and/or programmed to control the digital to analog conversion hardware so that the common reference is the first analog output, and wherein the first analog output corresponds to a particular one of the plurality of electrodes.

In one embodiment, the received digital information from an ECG machine utilizes electric potentials between pairs of the plurality of electrodes (e.g., for leads I, II and III) and electric potentials between an individual electrode of the plurality of electrodes as well as a reference electric potential involving a group of the plurality of electrodes such as, for example, Wilson's Central Terminal (e.g., for leads V1-V6) or one side of Einthoven's triangle (e.g., for leads aVR, aVL and aVF) whereas in the predetermined optimal format the system is operable for first controlling the digital conversion process and then the digital to analog conversion process to change the reference electric potential from any group of electrodes to the first analog output.

In an embodiment, a particular one electrode (i.e., a first electrode) of the plurality of electrodes could be an electrode placed on a limb of the living creature. In another embodiment, the plurality of electrodes may comprise a plurality of limb electrodes. The plurality of limb electrodes may comprise a right arm electrode, a left arm electrode, a right leg electrode, a left leg electrode, or any combination thereof. The second analog output may correspond to another particular one electrode (i.e., a second electrode) of the plurality of electrodes comprising a second limb of the living creature.

In another embodiment, the predetermined voltage on the second analog output with respect to the common reference may or may not comprise a zero voltage. The imposition of a zero voltage to second analog output comprises a direct connection from the second analog output to the common reference. The direct connection comprises a connection from the second analog output to the common reference through a resistor utilized for impedance matching.

In one embodiment, the plurality of electrodes comprises a plurality of limb electrodes and a plurality of precordial electrodes configured to produce an ECG recording, and the plurality of analog outputs correspond to the plurality of limb electrodes and the plurality of precordial electrodes. The digital information is produced by a first ECG machine made by a first manufacturer, and further comprising a plurality of connections connecting the plurality of analog outputs to a second ECG machine made by a second manufacturer.

In one embodiment, a first ECG machine is operable for producing a first analysis of the ECG recording, and a second ECG machine is operable for producing a second analysis of the ECG recording. In other words, the plurality of analog outputs is connectable to produce a plurality of analyses from different ECG machine manufacturers.

Another embodiment of the present invention may include a method for analyzing data produced by a first ECG machine that utilizes a plurality of electrodes and a reference comprising signals from at least two (i.e., a group) of the plurality of electrodes to produce a plurality of original lead signals, comprising receiving digital data from the first ECG machine and reconstructing a plurality of analog signals from the digital data from which can be obtained substantially identical lead signals as compared to the original lead signals produced by the first ECG machine, wherein a first of the plurality of analog signals comprises a new reference, and wherein an average RMS or other voltage or amplitude difference between the plurality of original lead signals and the substantially identical lead signals is calculated.

The method may comprise utilizing the plurality of the analog signals for producing an analysis of the substantially identical lead signals by a second ECG machine. The first of the plurality of analog signals corresponding to a first limb electrode. The method may further comprise imposing a predetermined voltage on a second of the plurality of analog signals and the second of the analog signals corresponds to a second limb electrode. In one possible embodiment, the predetermined voltage is zero with respect to the new reference.

BRIEF DESCRIPTION OF THE DRAWINGS

A more complete understanding of the invention and many of the attendant advantages thereto will be readily appreciated as the same becomes better understood by reference to the following detailed description when considered in conjunction with the accompanying drawings, wherein.

The above general description and the following detailed description are merely illustrative of the generic invention, and additional modes, advantages, and particulars of this invention will be readily suggested to those skilled in the art without departing from the spirit and scope of the invention.

DETAILED DESCRIPTION OF THE PREFERRED EMBODIMENT

The present invention comprises optimized methods and hardware configuration that accurately and effectively convert digital ECG data collected on one ECG machine manufacturer's hardware to analog, and then reconstructs the analog multichannel ECG data for insertion into another manufacturer's ECG machine for automated second opinions.

Figure 3:
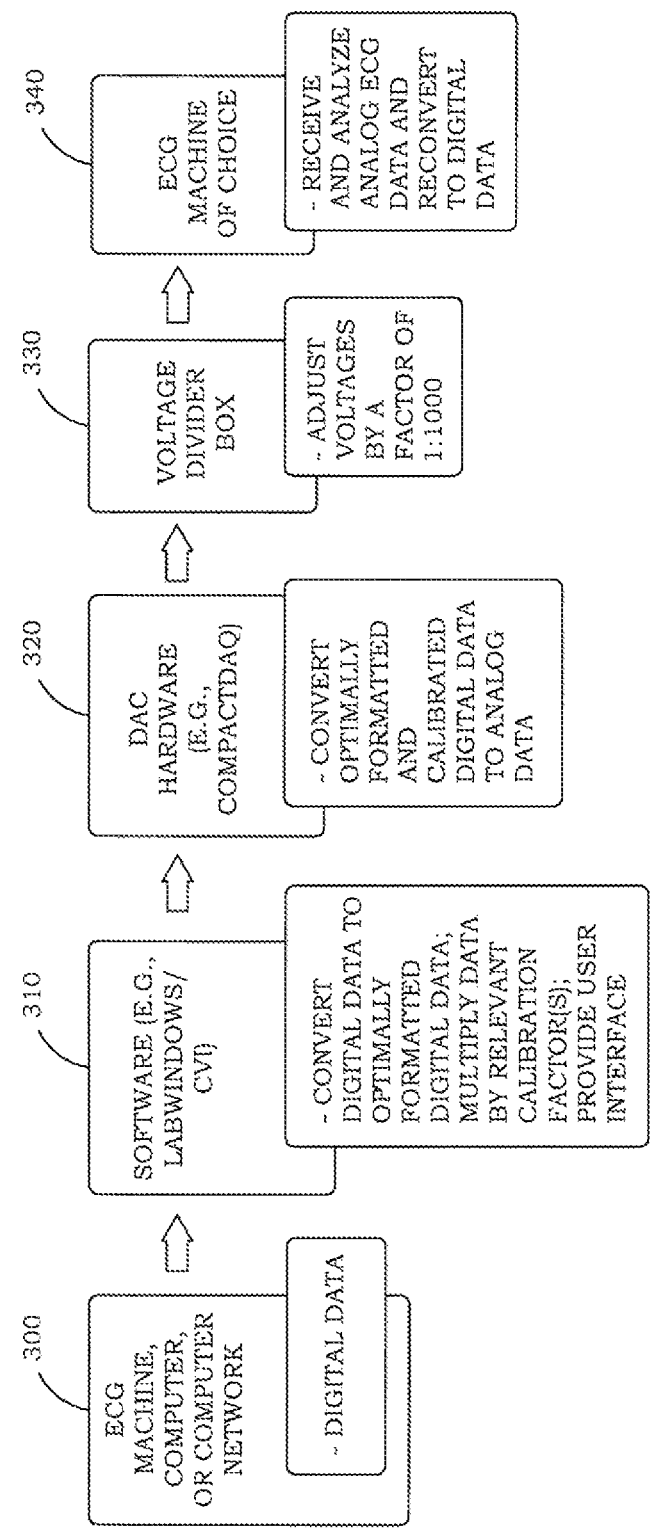
FIG. 3 is a schematic diagram of the digital to analog conversion and analog to digital conversion of ECG data in accord with one possible embodiment of the present invention.

Referring generally to FIG. 3, which is discussed in more detail below, the present invention is designed to begin with digital data, stored, streaming, or scanned in from ECG printouts as indicated at 300, that has been converted to an open digital format (provided hereinafter) optimized for the task of reproducing nearly identical original analog ECG signals. Once the original analog signals are reproduced, the system can move those signals forward into any manufacturer's ECG machine(s) to be re-digitized (or "reconstructed") there as indicated at 340. Thus automated diagnostic interpretations from multiple manufacturers' ECG machines can be obtained for any single ECG data file or stream, either locally or remotely, and with any desired degree of fidelity dependent only on the specifications of the "front end" ADC used for the original data collection.

From a practical standpoint, the described system will facilitate the construction and use for data collection of very inexpensive 12-lead ECG hardware front ends at remote sites including for example by patients at home or by third world practitioners who can use inexpensive cell phone or tablet devices to rapidly forward digital data to (and receive automated reports back from) remote server or cloud-based analytical sites. Because the ECG machines most commonly utilized in Western countries today are usually cost-prohibitive to employ in a "commodity" fashion, the use of the system described herein might result in significant cost savings to both governmental medical funding entities and humanitarian organizations. Under such a scenario, the aforementioned more expensive and bulky traditional ECG machines could instead be employed merely singly on the "back end", specifically at an ECG telemedicine central server site or within a cloud-based equivalent.

The system described herein was also specifically designed for processing ECG data collected in certain remote places wherein the main limitation may not be cost per se but rather the amount of allowable mass/volume and/or of locally available expertise, for example for 12-lead ECG data arriving from space or from remote terrestrial environments such as mobile military units, oil platforms or mountaineering, polar or other expedition areas. The present invention is not limited to 12 lead ECG machines or ECG machines in general but is applicable to other types of machines that involve collection of signals from electrodes placed on living creatures.

Figure 1:
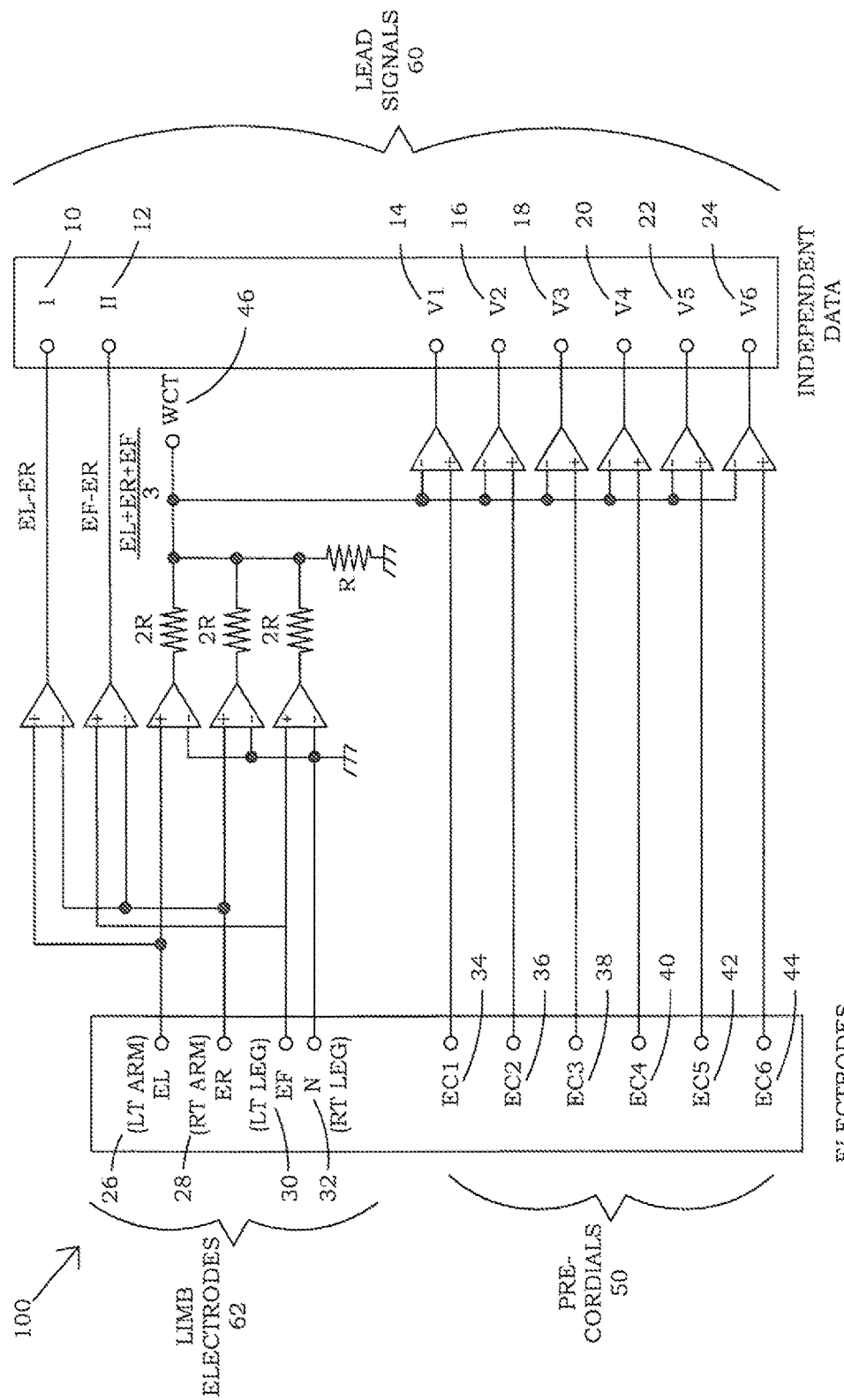
FIG. 1 is a functional diagram of a standard 12-lead electrocardiogram system, referenced to Wilson's Central Terminal, as utilized in typical ECG configurations.
Figure 2:
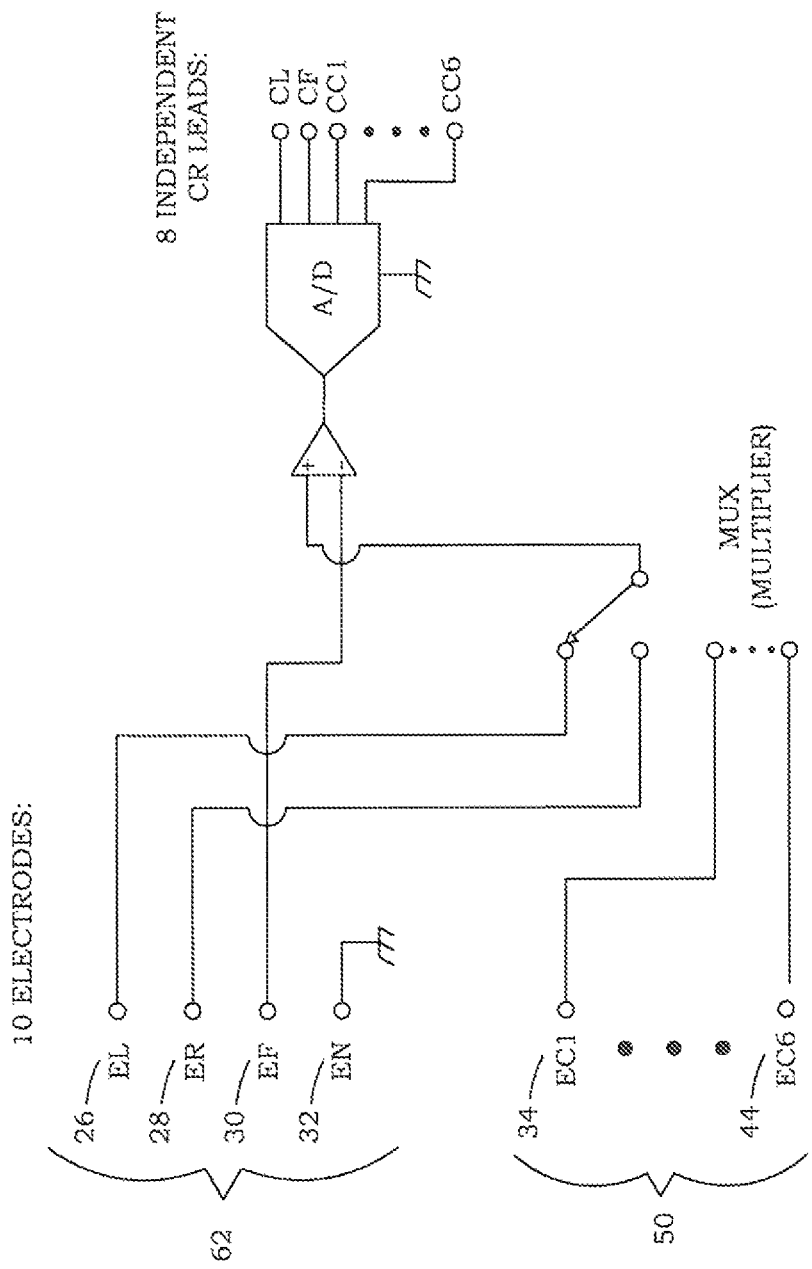
FIG. 2 is another functional diagram of a 12-lead electrocardiogram system as utilized in a typical ECG configuration.

Referencing FIG. 1, a functional diagram of a typical 12-lead electrocardiogram system 100 is depicted. When collecting standard 12-lead ECG 100, ten electrodes placed on the patient are used to obtain up to 9 different analog voltages, which are sometimes referred to as leads. These are voltages measured between various electrodes as discussed below. For a standard 12-lead ECG, ten electrodes may be placed on a living creature, which include limb electrodes 62 and precordial electrodes 50. Various types of ECG systems and other systems for measuring voltages from machines may be utilized in accord with the present invention. However, the present invention is described in terms of the standard 12-lead ECG. FIG. 2 shows another simplified 12 lead ECG system wherein the multiplexor and analog to digital signal converter are shown.

The limb electrodes 62 may comprise left arm electrode 26, right arm electrode 28, left leg electrode 30, right leg electrode 32, or any combination thereof. It is of note that in this situation right leg electrode 32 is used only as a voltage common for generating the nine independent analog voltages. Additionally, precordial electrodes 50 are typically placed surrounding a patient's chest and include 6 electrodes, i.e., EC1 electrode 34, EC2 electrode 36, EC3 electrode 38, EC4 electrode 40, EC5 electrode 42, and EC6 electrode 44.

The measured voltage differences (i.e., signals) between the electrodes are stored digitally as independent data leads 60, which most often include lead I 10, lead II 12, and leads $V_1$-$V_6$, 14-24, as referenced to Wilson's Central Terminal, or WCT 46 wherein the Wilson's Central Terminal is commonly known in the art. If one defines the original ten electrodes as follows: left arm=EL; left leg=EF; right arm=ER; right leg=N (reference neutral) and chest=$EC_i$(i=1-6), then the independent data leads 60 would most commonly be expressed as:

$I=EL-ER;$ $II=EF-ER;$ $V_i=EC_i-WCT;$ $WCT=(EL+ER+EF)/3.$

As discussed herein, ECG machines are typically only capable of receiving analog data to operate as intended. Once the information (i.e., signals) is stored digitally as outlined above, the problem encountered becomes how the eight independent data leads can be utilized to produce at least nine DAC channels, once uncoupled from WCT 46 provided on the original ECG machine (because the final receiving ECG machine is itself again expected do such coupling), that will produce data lead I 10, data lead II 12, and data leads $V_1$-$V_6$, 14-24, at the receiving ECG machine. To solve the problem, the reconstructed lead signals should appear as if the DAC channels had come from limb electrodes 62 and precordial electrodes 50 used on a patient to generate these data channels, essentially simulating the measurements that were previously made on a living creature, such as a live patient. In an embodiment and in accord with the present invention, as explained herein, for a 12-lead ECG system that utilizes a digital file format wherein the chest electrodes are referenced to WCT, a digital transformation is first performed wherein the chest electrodes are instead referenced to the right arm electrode (i.e., to ER, thereby producing "CRi" instead of "Vi" chest lead data).

FIG. 1 expresses the problem graphically by showing a generalized functional diagram for a typical 12-lead ECG system, but ignoring (as defined) the non-independent leads III, aVR, aVL and aVF.

In one possible embodiment of the present invention, for any 12-lead ECG system that utilizes a digital format, the format is first changed if necessary to one in which the chest electrodes are referenced not to WCT, but instead to an electrode, such as a limb electrode. In one possible example, the right arm electrode is utilized.

Accordingly, with reference to right arm electrode 28 (i.e., to ER, thereby perhaps better distinguished in terminology by producing "$CR_i$" instead of "$V_i$" chest lead data), the following applies:

$CR_i=EC_i-ER;$

Figure 4:
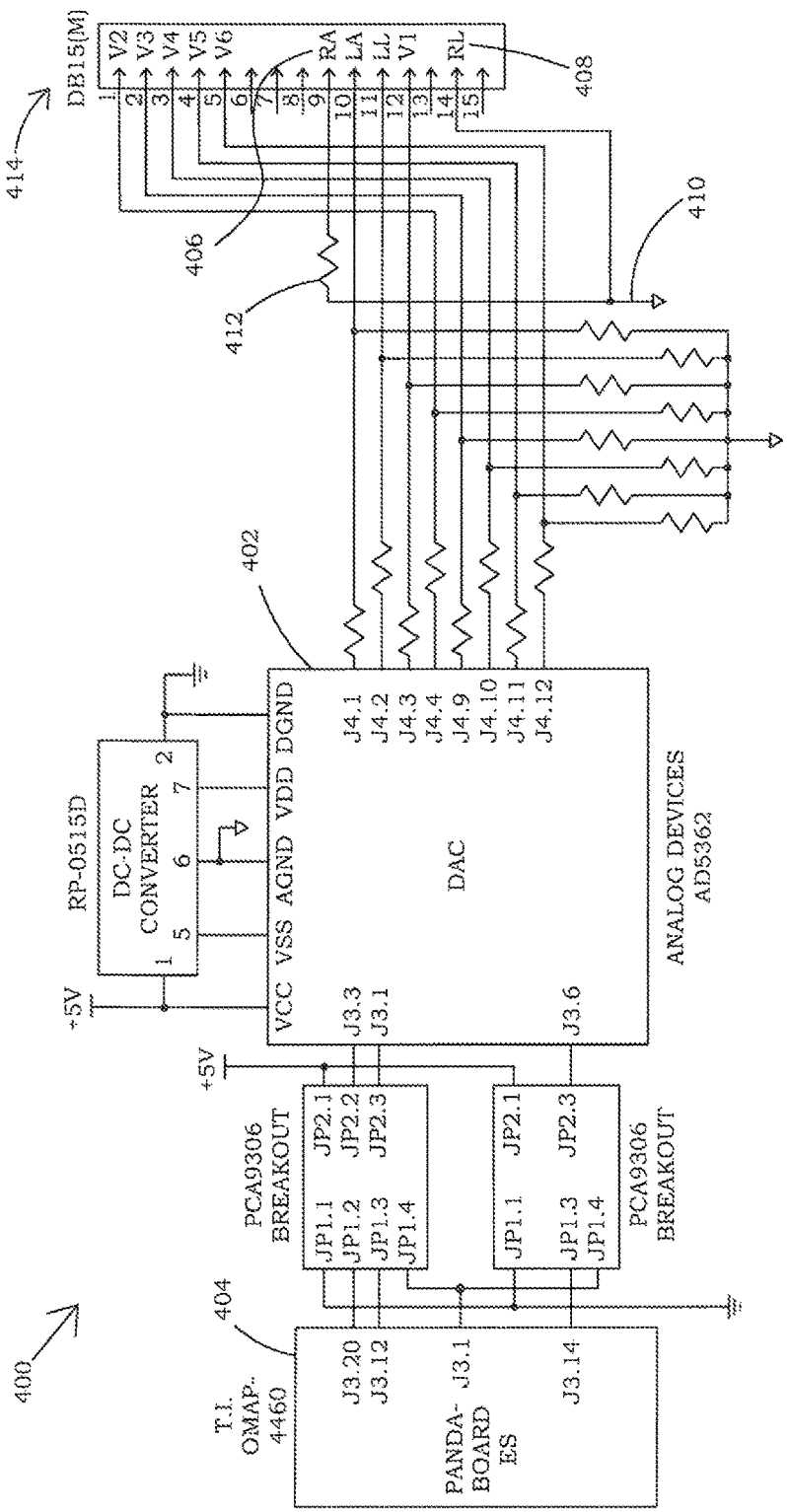
FIG. 4 is a device that may be utilized as part of reconstruction of analog signals from digitized signals of different ECG machine manufacturers in accord with one embodiment of the present invention.

Referring to FIG. 4, DAC (see generally DAC 402 in FIG. 4) receives the optimally formatted digital data from control 404 for representative digital data to provide a means to convert back to substantially original leads.

In one possible example, a "zero" voltage can be imposed upon its right arm electrode input, i.e., what might be termed "ER0". A possible example of this is seen in circuit form of FIG. 4, where analog output 406, which is conveniently labeled RA, but corresponds to ER, is tied to zero. The zero voltage of RA could be imposed by software but in this case is done in hardware. Resistor 412 is provided for impedance matching purposes. So at this time the analog signal RA is zero volts with respect to the analog output neutral 408, conveniently referred to as RL that corresponds to the right leg electrode, that is provided as the neutral or ground as indicated at 410. So now the algebra discussed above is transformed in a way that allows substantially original lead signals to be reconstructed. Specifically, going through the algebraic description again so that RA has been tied to zero with respect to the neutral:

$I=EL;$ $II=EF;$ $CR_i=EC_i;$ and $WCT=(1+II)/3.$

Therefore, if the following conditions are assigned to DAC 402, they should ultimately produce, on most if not all ultimately receiving (re-digitizing) 12-lead ECG machines, the desired I, II, and $V_1$-$V_6$ data lead signals:

0 volts on the right arm electrode input ER (also referred to as RA);

Lead I signal on the left arm electrode input EL;

Lead II signal on the left leg electrode input EF;

DAC common on the right leg electrode input N;

$CR_i$ signals derived from $V_i$ channels on the precordial electrode inputs $EC_i$.

In other words, referring to analog outputs 414 in FIG. 4, the lead signals can be recreated from the ten analog outputs, which are conveniently labeled as they would be if they were actual electrodes on the living creature.

Other aspects of the present invention are of interest to those skilled in the art. First, in the example provided, the chest electrodes are referenced not to WCT, but instead to the right arm electrode, a system originally favored by original persons of interest in the ECG field, such as Einthoven. Other persons in the 12 lead ECG field also favored such a reference, even after the introduction of WCT in the 1930s. While the above is one embodiment of the invention, it is also possible to accomplish the same fundamental end point through a digital format wherein all other electrodes are referenced to the left arm electrode while a zero voltage is simultaneously imposed on the DAC 402 left arm electrode input, or through a digital format wherein all other electrodes are referenced to the left leg electrode while a zero voltage is simultaneously imposed on the DAC left leg electrode input. Accordingly, the present invention is not limited to the particular assignments of neutral and/or application of zero volts to analog outputs representative of electrode signals as described above. Additionally, while tying analog output 406 to the neutral as described above for imposition of zero volts, which presently appears convenient, conceivably other predetermined voltages might also be utilized. So the invention is not limited to the presently described embodiment. With the ten electrode signals recreated, it is now possible to produce the reconstructed lead signals.

However, this format is not exclusive for the present invention to function as intended. As described below, two alternate reference electrode scenarios are mathematically depicted supposing, for example, that EL or EF is used as a reference instead of ER.

With EL as the reference, then:

$CR=ER-EL=-I$ $CF=EF-EL=III;$ $CC_i=EC_i-EL;$ $II=CF-CR=III+1;$ $V_i=EC_i-(ER+EF+EL/3);$ $V_i=CC_i-(CR+CF)/3.$

With EF as the reference, then:

$CL=EL-EF=-III;$ $CR=ER-EF=-II;$ $CC_i=EC_i-EF;$ $I=CL-CR;$ $V_i=(3EC_i-ER-EL-EF)/3;$ $V_i=EC_i-(CR+CL)/3.$

Figure 5:
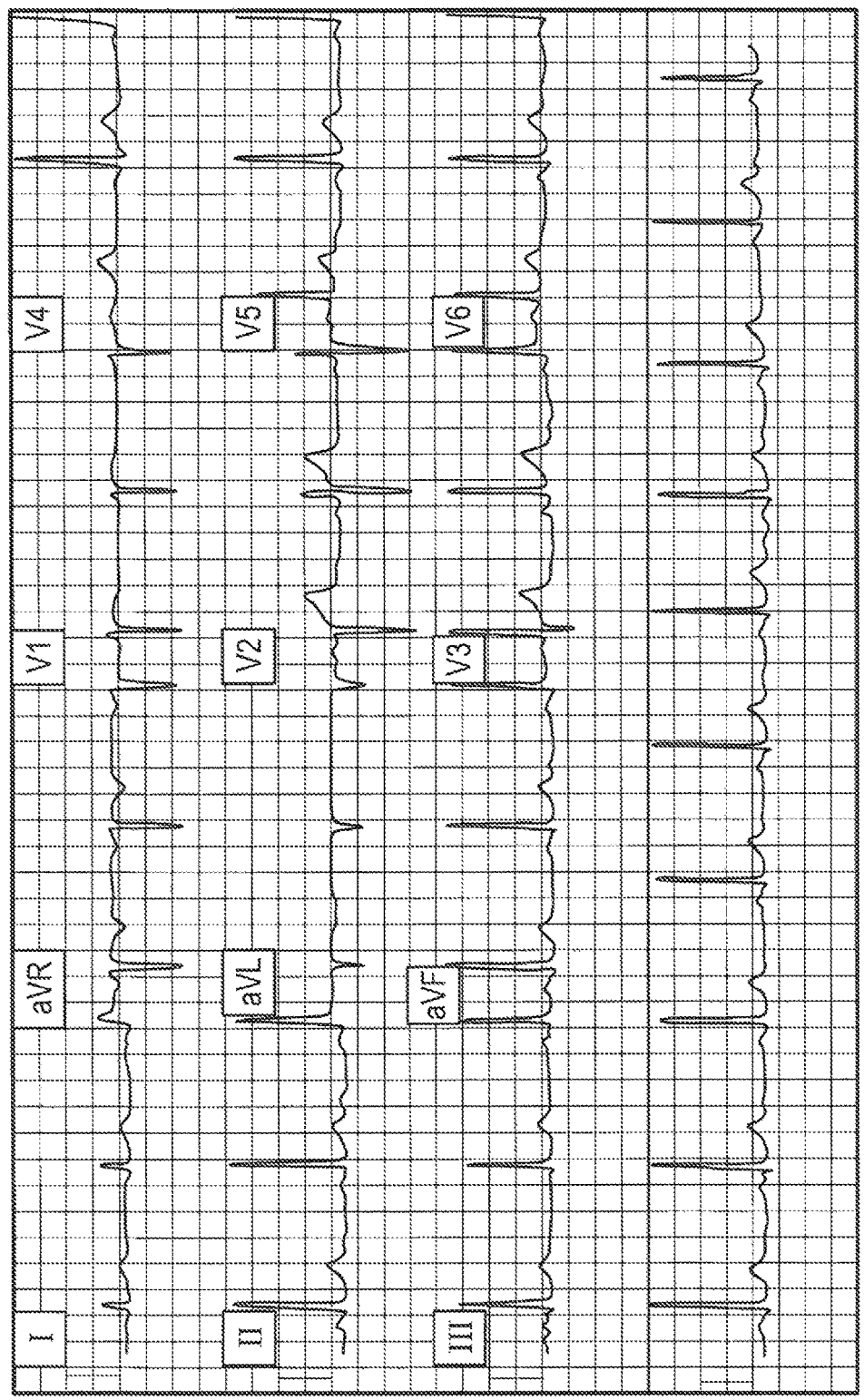
FIG. 5 is an original ECG report as described hereinafter.
Figure 6:
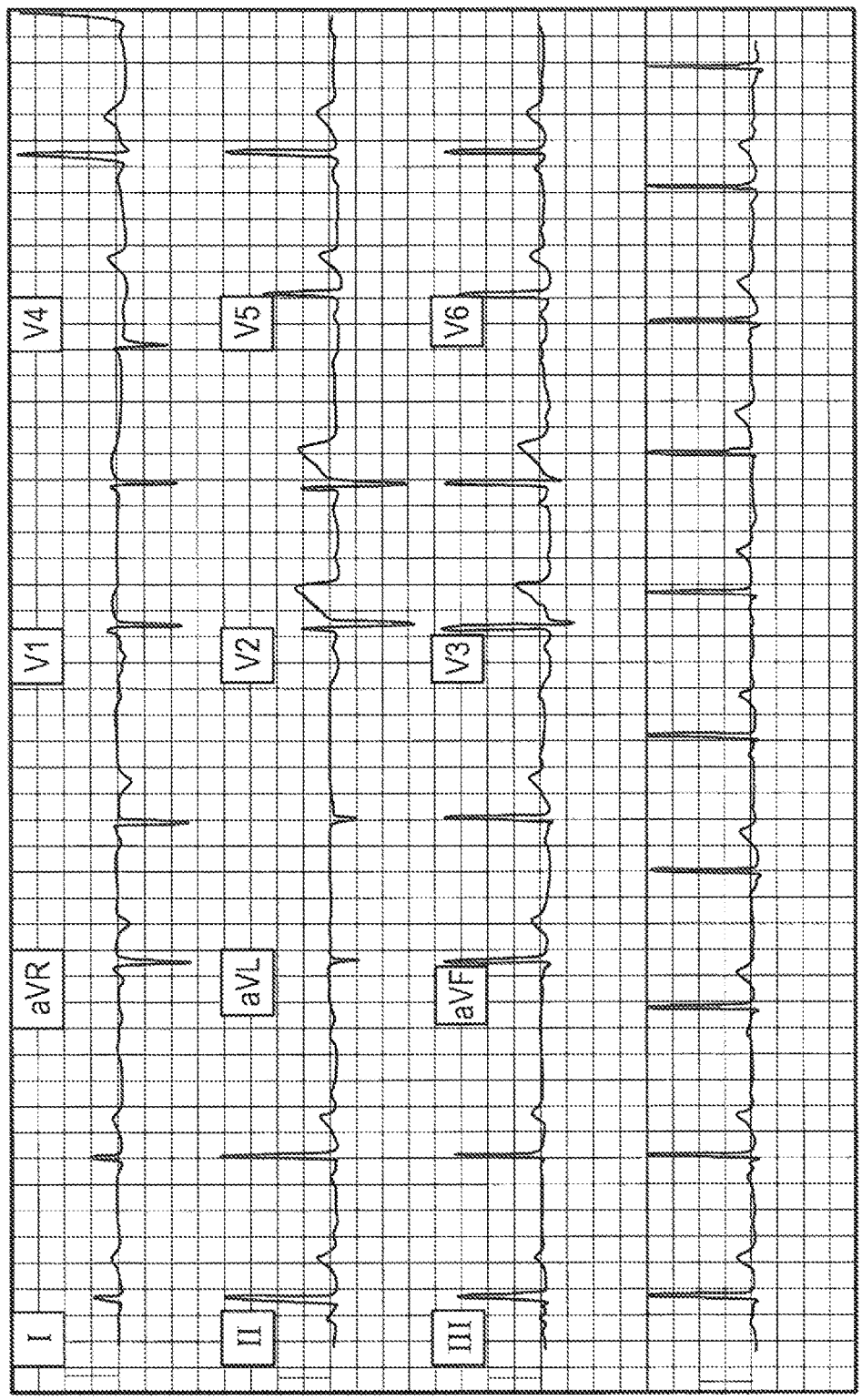
FIG. 6 is a reconstructed ECG report of the original ECG report of FIG. 5 in accord with one possible embodiment of the present invention.
Figure 7:
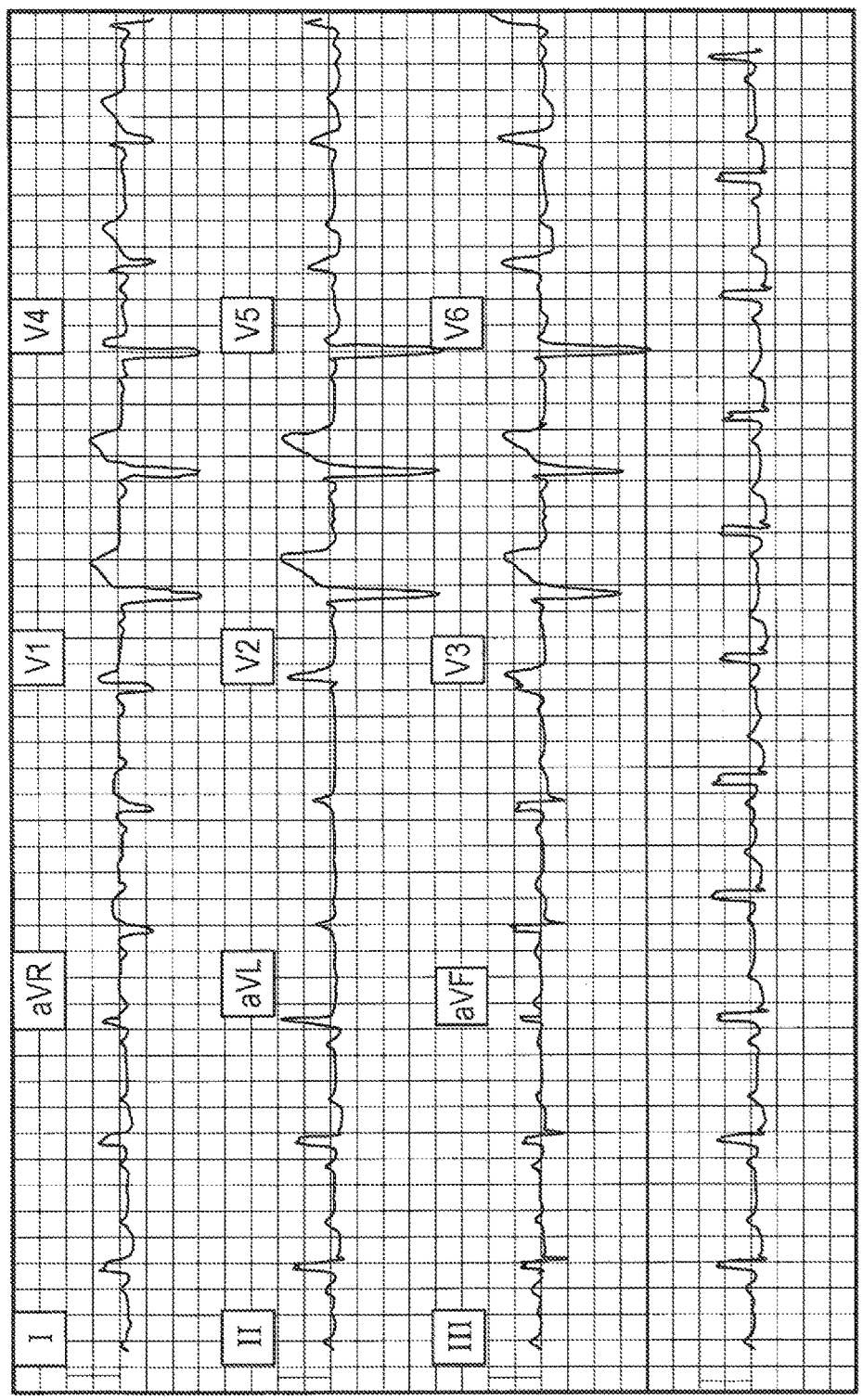
FIG. 7 is a second original ECG report as described hereinafter.
Figure 8:
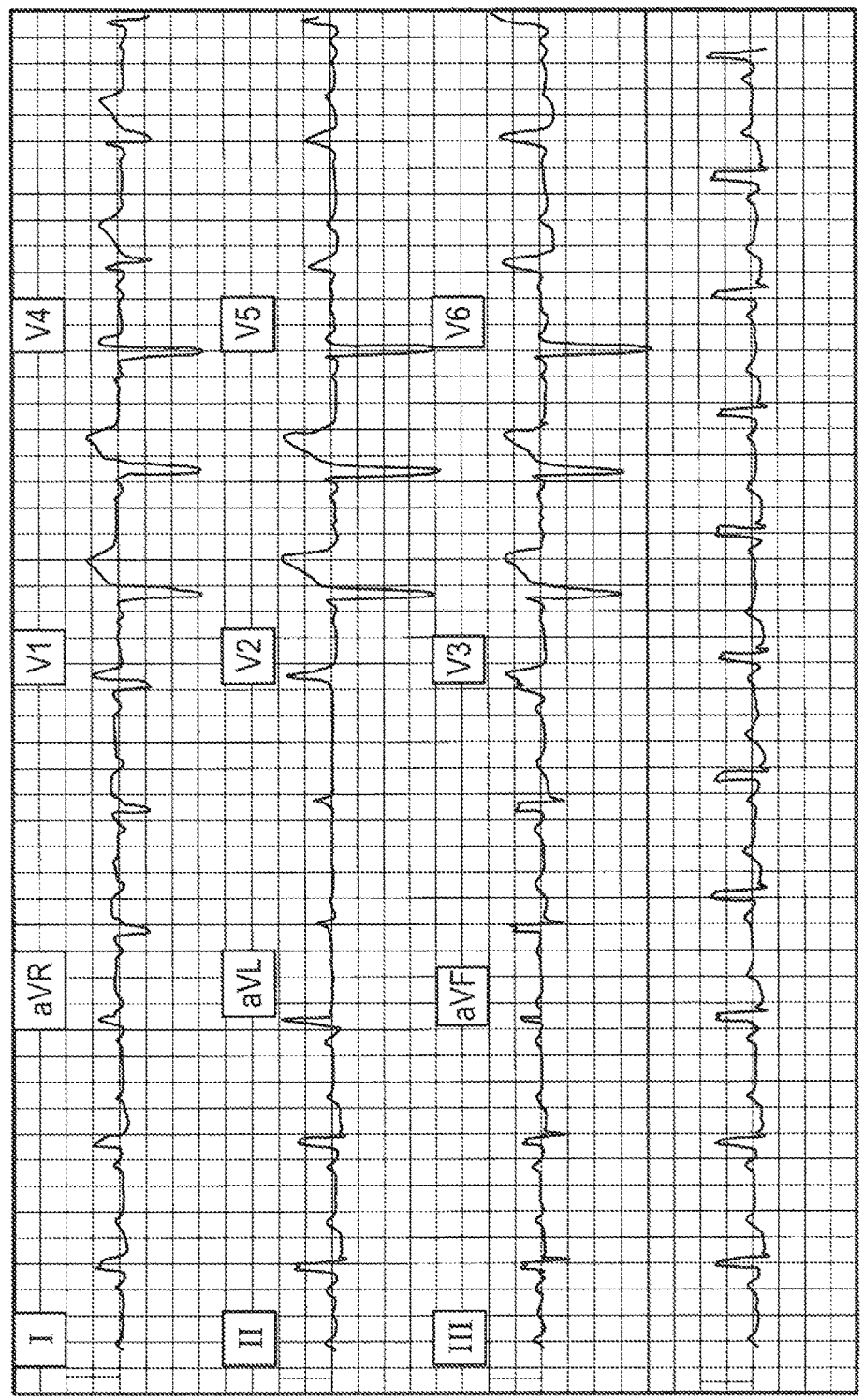
FIG. 8 is a reconstructed ECG report of the original ECG report of FIG. 5 in accord with one possible embodiment of the present invention.

As discussed in more detail hereinafter, FIGS. 5 and 7 show original signals and FIGS. 6 and 8 show the reconstructed lead signals. It will be appreciated that visually the signals look substantially identical.

Various types of validation studies have been made.

Ten 12-lead ECG data files, each between 5-10 min in length, that were previously collected from five healthy and five diseased patients, respectively, using a high-fidelity, 1000 samples/sec 12-lead PC-ECG device (Cardiax, IMED Ltd., Budapest, Hungary), were randomly selected from a large set of pre-existing files to help validate the system. The 12-lead ECGs were clinically normal in each of the five healthy patients, whereas in the five diseased patients, the following electrocardiographic conditions were respectively selected (from affected individuals chosen at random) in order to include a wide range of electrocardiographic pathologies: 1) Coronary artery disease without prior myocardial infarction and with normal QRS interval; 2) Coronary artery disease with prior myocardial infarction (i.e., ischemic cardiomyopathy) but with normal QRS interval; 3) Non-ischemic (dilated) cardiomyopathy with normal QRS interval; 4) Left bundle branch block of uncertain etiology; and 5) Right bundle branch block of uncertain etiology.

Validation studies were performed to compare the original digital ECG data to their reconstructed (i.e., after DAC and repeat ADC) counterpart data including quantitative and qualitative studies. Quantitative validation studies compared the total-waveform voltage differences between the original and reconstructed data while the second type qualitatively compared the automated electrocardiographic (i.e., clinical) diagnostic statements generated by the original versus reconstructed data.

For quantitative validation, a MATLAB®-based script was written to superimpose the data in the original and reconstructed files for each subject by using the corresponding R-wave fiducial point locations in the files to align the corresponding waveforms. Each test file had 250-500 PQRST complexes within a 5-10 min data epoch. For each PQRST complex, a region about the R-wave fiducial point was detrended and the original versus reconstructed waveforms were overlaid and shifted to minimize the root mean square (RMS) difference. The standard deviation was used as a proxy because detrending alone ensures a near zero mean but not a perfectly zero mean. An average RMS difference estimate across all beats was then calculated for each channel in each patient, as was an overall average RMS difference for all channels combined. This same process was performed twice: once after having used the same model of ADC (Cardiax 12-lead ECG recorder) to collect the reconstructed (re-digitized) data that had also been used to collect the original data; and once after having used a different manufacturer's ADC recorder (BT 12, CorScience, Erlangen. Germany) to collect the re-digitized data.

TABLE 1

| Subject | Channel: | | | | | | | |
|---|---|---|---|---|---|---|---|---|
| | I | II | CR1 | CR2 | CR3 | CR4 | CR5 | CR6 |
| 1H | 5.2 | 6.6 | 5.8 | 14.4 | 10.4 | 9.9 | 9 | 8.4 |
| 2H | 2.8 | 6.8 | 4.2 | 13.6 | 9.1 | 9.6 | 8.3 | 8 |
| 3H | 3 | 7.4 | 4.1 | 8 | 7.1 | 11.7 | 10.8 | 9.6 |
| 4H | 7.1 | 8 | 7.4 | 13.2 | 9.9 | 9.2 | 9.4 | 9.2 |
| 5H | 3.4 | 5.3 | 2.8 | 8.3 | 10.7 | 8.7 | 6.8 | 5.8 |
| 1D | 2.2 | 3.5 | 3.3 | 6 | 8 | 5.1 | 4.7 | 4.7 |
| 2D | 4.2 | 3 | 7.1 | 6.5 | 4.2 | 4.2 | 4.3 | 4.6 |
| 3D | 3.2 | 3.2 | 5.6 | 8.3 | 7 | 5.7 | 5.5 | 5.5 |
| 4D | 8.9 | 10.7 | 18.2 | 29.6 | 23 | 13.2 | 11.4 | 17 |
| 5D | 12.5 | 13.8 | 9.7 | 13.9 | 15.1 | 15.2 | 16.7 | 14.7 |

For the quantitative validation, voltage comparisons are made. Table 1 shows the estimated RMS difference values for each of the eight independent ECG channels (PQRST) when the same model of ADC recorder (Cardiax) that had been used to collect the original data was also used to collect the re-digitized data. Under these circumstances, the grand-average (SEM) RMS difference value between the original and re-digitized data was 8.5±0.05 ADC counts per channel, or equivalently 20.8±0.12 microvolts.

TABLE 2

| Subject | Channel: | | | | | | | |
|---|---|---|---|---|---|---|---|---|
| | I | II | CR1 | CR2 | CR3 | CR4 | CR5 | CR6 |
| 1H | 5.3 | 6.9 | 6.2 | 10.4 | 9.5 | 9.5 | 9.2 | 8.6 |
| 2H | 6.6 | 11.1 | 8.6 | 12.8 | 17.6 | 13.6 | 12.3 | 11.4 |
| 3H | 8.3 | 9.7 | 8.7 | 15.7 | 11.3 | 13.6 | 12 | 11.2 |
| 4H | 4.6 | 6.6 | 6 | 10.6 | 8.1 | 8.5 | 8.6 | 7.6 |
| 5H | 6.3 | 9.4 | 7.1 | 9.9 | 12.7 | 11.1 | 9.8 | 8.7 |
| 1D | 6.2 | 8.9 | 8.1 | 11.2 | 10.8 | 10.6 | 9.8 | 8.5 |
| 2D | 11.5 | 11.6 | 13.2 | 13.9 | 15.2 | 15.7 | 15.4 | 14.2 |
| 3D | 6.3 | 5.9 | 6.1 | 8.5 | 9 | 10.6 | 10.8 | 8.4 |
| 4D | 10.8 | 18.3 | 21.5 | 37.3 | 27.8 | 17.3 | 19.4 | 26.3 |
| 5D | 12.7 | 14.5 | 11.6 | 13.5 | 15.4 | 16.4 | 18.1 | 15.4 |

Table 2 shows the estimated RMS difference values for each of the eight independent ECG channels (PQRST) when the re-digitized data were instead collected on an ADC (i.e., CorScience) that was different from the ADC (Cardiax) used to collect and store the original data. Under these circumstances, the grand-average RMS difference values between the original and re-digitized data was 11.6±0.08 ADC counts per channel, or equivalently 28.4±0.21 microvolts.

As can be surmised from Tables 1 and 2, there were no clear trends in the differences generated by the original versus re-digitized files in the healthy versus diseased subjects when the QRS interval was within a clinically normal range. However, as might be expected, the presence of either left (subject 4D) or right (subject 5D) bundle branch block, wherein the QRS interval is relatively prolonged and the total voltage relatively increased, tended to increase the differences between the voltages in the original versus re-digitized files.

A more qualitative (clinical) validation was also performed to further validate system performance. The qualitative validation involves automated clinical diagnostic systems used by ECG machine manufacturer. Specifically, the automated diagnostic statements produced by commercial electrocardiographic software for the data within the first 15 seconds in the original files were compared in each case to the automated diagnostic statements produced for the same data in the post-DAC re-digitized files. Such analyses of potential changes in automated diagnostic statements were in turn performed in three separate ways: 1) by using the automated diagnostic program native to the Cardiax software program when the Cardiax model of ADC recorder had been used to collect both the original and re-digitized data; 2) by using the well-validated Leuven automated diagnostic program for both the original data and the re-digitized data when the Cardiax model of ADC recorder had been used to collect both the original and re-digitized data; and 3) by again using the Leuven automated diagnostic program for both the original data and for the re-digitized data when the Cardiax recorder had been used to collect the original data but the CorScience recorder the re-digitized data.

TABLE 3

| Subject | Original File | Re-digitized File |
|---|---|---|
| 1H | No signs of abnormalities given the patient's age. | No signs of abnormalities given the patient's age. |
| 2H | Sinus rhythm; 1 premature sinus complex. | Sinus rhythm; 1 premature sinus complex. |
| 3H | Corresponds to the following pathological abnormality: undetermined rhythm | Corresponds to the following pathological abnormality: undetermined rhythm |
| 4H | No signs of abnormalities given the patient's age. | No signs of abnormalities given the patient's age. |
| 5H | No signs of abnormalities given the patient's age. | No signs of abnormalities given the patient's age. |
| 1D | Sinus rhythm; suggests the following possible abnormality: left atrial enlargement. | Sinus rhythm; suggests the following possible abnormality: left atrial enlargement. |
| 2D | Sinus rhythm; corresponds the following possible abnormality: first-degree AV block (Long PQ); undetermined variation: T wave abnormality | Sinus rhythm; corresponds the following possible abnormality: first-degree AV block (Long PQ); undetermined variation: T wave abnormality |
| 3D | No signs of abnormalities given the patient's age. | No signs of abnormalities given the patient's age. |
| 4D | Sinus rhythm; suggests the following possible abnormality: left bundle branch block. | Sinus rhythm; suggests the following possible abnormality: left bundle branch block. |
| 5D | Sinus rhythm; suggests the following possible abnormality: right bundle branch block. | Sinus rhythm; suggests the following possible abnormality: right bundle branch block. |

Table 3 shows the automated clinical diagnostic statements outputted by the commercial Cardiax software program for all ten cases when both the original and re-digitized files were collected on the same model of Cardiax ADC. As can be surmised from Table 3, for all ten cases, under these circumstances, there were no differences in the clinical diagnostic statements outputted by Cardiax for the original versus the re-digitized files.

TABLE 4

| Subject | Original File | Re-digitized File |
|---|---|---|
| 1H | Sinus arrhythmia; normal morphology | Sinus arrhythmia; normal morphology |
| 2H | Sinus bradycardia; normal morphology | Sinus bradycardia; abnormal re-polarization, possibly non-specific; QRS within the normal limits |
| 3H | Sinus arrhythmia; abnormal re-polarization, possibly non-specific; QRS within the normal limits | Sinus arrhythmia; abnormal re-polarization, possibly non-specific; QRS within the normal limits |
| 4H | Sinus bradycardia; normal morphology | Sinus bradycardia; normal morphology |
| 5H | Normal sinus rhythm; normal morphology | Normal sinus rhythm; normal morphology |
| 1D | Normal sinus rhythm; normal morphology | Normal sinus rhythm; normal morphology |

TABLE 4-continued

| Subject | Original File | Re-digitized File |
|---|---|---|
| 2D | Sinus rhythm with first-degree AV block; left atrial hypertrophy; abnormal re-polarization, possibly non-specific; QRS within the normal limits | Sinus rhythm with first-degree AV block; left atrial hypertrophy; abnormal re-polarization, possibly non-specific; QRS within the normal limits |
| 3D | Normal sinus rhythm; possible inferior infarction, possibly old | Normal sinus rhythm; possible inferior infarction possibly old |
| 4D | Sinus rhythm; complete left bundle branch block | Sinus rhythm; complete left bundle branch block |
| 5D | Sinus rhythm; ventricular extrasystole(s); ventricular extrasystole(s) with full compensation; complete right bundle branch block | Sinus rhythm; ventricular extrasystole(s); ventricular extrasystole(s) with full compensation; complete right bundle branch block |

Table 4 shows the automated clinical diagnostic statements outputted by the commercial Leuven software program for all ten cases when the original files were collected on the Cardiax ADC and when the re-digitized files were collected on either the Cardiax or CorScience ADC (i.e., the ultimate interpretive results from the Leuven program were the same under both of the above circumstances). Under either of these circumstances, the automated diagnostic statements outputted by the Leuven program for the original versus the re-digitized files differed for only one case (i.e., for healthy patient 2H). Specifically, within the Leuven program, criteria for "abnormal re-polarization, possibly non-specific" were triggered for patient 2H's re-digitized file whereas such criteria were not triggered for this same patient's original file. While it is unclear whether this minor difference in the Leuven algorithm's automated interpretation would have made any clinical difference (it is suspected this is not the case), the original and re-digitized ECGs for this patient as interpreted by the Leuven algorithm are shown in FIG. 5 and FIG. 6. Both FIG. 5 and FIG. 6 (which shows the corresponding "worst-case comparison" between original and re-digitized files as quantified by the greatest differences in RMS values; patient 4D) also aptly demonstrate the very minor differences that typically occurred between all original versus re-digitized files with respect to the various electrocardiographic axes, intervals and voltages that were outputted by the automated interpretive software.

These results suggest that the system described herein can reproduce original analog signals from stored 12-lead ECG data files with a degree of fidelity likely sufficient for most clinical applications. The overall greater utility and flexibility, more open format, and "readiness for cloud computing" of the system of the present invention potentially open up several new avenues for more widespread use of DAC devices in clinical electrocardiography. Specifically, systems such as those presented herein might eventually allow for all of the following:

1) rapid second opinions from any number of automated interpretive programs, e.g., for difficult-to-interpret 12-lead ECGs and rhythms (not only locally, but also from dedicated remote central servers or "the cloud");

2) use of less expensive (i.e., commodity-style) 12-lead ECG front ends (ADC hardware) in impoverished or undeserved areas, since subsequent DAC permit use of any preferred (or any otherwise prohibitively-expensive) ECG machine or interpretive program only singly, on the "back end";

3) use of less bulky ECG front ends during space flight or in remote terrestrial environments such as military mobile units, oil platforms or in mountaineering, polar or other expedition areas;

4) improved performance of all automated ECG analytical software programs through the implementation by manufacturers of those "interpretive lessons learned" that will be more rapidly ascertainable to them both through internal testing and through objective competitions enabled by the DAC;

5) better within-hospital consistency of automated ECG interpretations, e.g., when ECG machines from multiple different manufacturers are used in any single institution;

6) better across-study consistency when large digital ECG databases are analyzed in epidemiological studies, since DAC should theoretically allow for the same analytical programs to be used, when desired, across all such large studies, even when different collaborating groups don't all possess the same hardware and software; and, finally for 7) furthering the potential clinical and archival utility of other technology that converts paper ECG printouts to digital ECG files.

Of note, the only prerequisite for the use of the described system is that the format of the original digital data should be known—i.e., to permit conversion into an optimal digital format for DAC—or, if not known, then alternatively convertible to that optimal format by an integrated or secondary software program tailored to making such conversions. Once the data are in an optimized format, then the System can be easily employed either locally or remotely to convert the digital data to analog and then in turn to stream the analog data into any desired 12-lead ECG device.

The following represents an optimized data format that may be used in conjunction with one possible embodiment of the present invention:

Header: Stored or other ECG data to be converted back to analog need not have a header.

Sample value: Although this can theoretically vary without great consequence, the sample value in the utilized format is a 16-bit signed integer, ranging from +2047 to −2048, in Intel byte order, meaning low byte first, or "little endian."

Format: The DAC device presently assumes that the incoming digital data will be in binary format, as one would obtain directly from a multiplexed ADC. In an embodiment, the specific format utilized is presented on a sample-by-sample basis further below. However, in a preferred embodiment, the preferred digital format is one wherein all given precordial electrodes are referenced not to Wilson's Central Terminal, but rather to a limb electrode, in an embodiment to the right arm electrode, making preferred precordial channels the "CR" channels rather than the "V" leads. Right arm electrode-referenced precordial channels are ideal for a pre-DAC digital format because the repeat ADC, by any given 12-lead ECG device that follows DAC, may then naturally convert the so-formatted precordial channel data back to the V precordial lead format using whatever scheme the given ECG manufacturer uses to accomplish that specific task for a traditional patient.

The Programming notes below provide further background information on how a right arm electrode-referenced 12-lead ECG data format can be accomplished in software and applied either to ADC, or, as in this specific embodiment, to an ideal digital format for pre-DAC.

Programming Notes:
9+1 channels, e.g., from the electrodes on a patient:
EL, EF, ER, EC1, EC2, EC3, EC4, EC5, EC6 (+N)
EL: left arm
EF: left leg
ER: right arm
N: right leg (reference neutral)
ECi: chest (precordial) leads
Measured (Raw Data):
(8 channels): CL, CF, CR1, ... , CR6

$$CL=EL-ER,\ CF=EF-ER,\ CR1=EC1-ER,\ \ldots,\ CR6=EC6-ER$$

The combined data are mathematically represented as described herein below:

$$I=EL-ER=CL$$

$$II=EF-ER=CF$$

$$III=EF-EL=(EF-ER)-(EL-ER)=CF-CL$$

$$aVR=ER-(EL+EF)/2=(2*ER-EL-EF)/2=-((EL-ER)+(EF-ER>>))/2=-(CL+CF)/2$$

$$aVL=EL-(EF+ER)/2=(2*EL-EF-ER)/2=(2*(EL-ER)-(EF-ER))/2=CL-CF/2$$

$$aVF=EF-(EL+ER)/2=(2*EF-EL-ER)/2=(2*(EF-ER)-(EL-ER))/2=CF-CL/2$$

$$Vi=ECi-(EL+EF+ER)/3=(3*ECi-EL-EF-ER)/3=(3*(ECi-ER)-(EL-ER)-(EF-ER))/3=(ECi-ER)-((EL-ER)+(EF-ER))/3=CRi-(CL+CF)/3$$

i=1 . . . 6

The binary data are thus constituted by I, II, and CR1-6 which represent eight independent data channels. Furthermore, $Vi=CRi-(I+II)/3$ and thus $CRi=Vi+(I+II)/3$. In an embodiment, $CRi=ECi$ if $ER=0$, which provides a basis for the optimized format used in the present system. Given the above information and definitions, an optimized data format that is ultimately input into the DAC device can be represented as follows:

| Sample (0): | Channel 1 = CL = Lead I | (2-bytes) | Bytes 0-1 |
| --- | --- | --- | --- |
| | Channel 2 = CF = Lead II | (2-bytes) | Bytes 2-3 |
| | Channel CR1 | (2-bytes) | Bytes 4-5 |
| | Channel CR2 | (2-bytes) | Bytes 6-7 |
| | Channel CR3 | (2-bytes) | Bytes 8-9 |
| | Channel CR4 | (2-bytes) | Bytes 10-11 |
| | Channel CR5 | (2-bytes) | Bytes 12-13 |
| | Channel CR6 | (2-bytes) | Bytes 14-15 |
| Sample (1): | Channel 1 = CL = Lead I | (2-bytes) | Bytes 16-17 |
| | Channel 2 = CF = Lead II | (2-bytes) | Bytes 18-19 |
| | Channel CR1 | (2-bytes) | Bytes 20-21 |
| | Channel CR2 | (2-bytes) | Bytes 22-23 |
| | Channel CR3 | (2-bytes) | Bytes 24-25 |
| | Channel CR4 | (2-bytes) | Bytes 26-27 |
| | Channel CR5 | (2-bytes) | Bytes 28-29 |
| | Channel CR6 | (2-bytes) | Bytes 30-31 |
| Sample (n): | Etc. | | |

The configuration referenced above provides an optimized data format easily transformed and reconfigured for use with a preferred embodiment of the present invention. Right arm electrode-referenced precordial channels are ideal for a pre-DAC digital format because as described herein, the repeat ADC by any given 12-lead ECG device that follows an appropriately configured DAC step may then naturally convert CR precordial channel data back to the V precordial lead format by using whatever scheme the given ECG manufacturer uses to accomplish that specific task on the instrumented human. As a result, this format is preferred for all ECG data before being sent to the receiving ECG machine for transformation.

Turning back to FIG. 3, a schematic diagram of the data processing method associated with the ECG data in accord with a preferred embodiment of the present invention is depicted. Step 300 is comprised of digital electrocardiogram data produced by an ECG machine, stored on a computer, and/or transmitted via a computer network. Step 310 converts digital data to optimally formatted digital data using software. In one embodiment, software can be preprogrammed with relevant calibration factors to multiply with the digital data based on the generating ECG machine utilized in producing the original digital data. Step 310 is responsible for changing the reference electrode from WCT to a limb electrode, as discussed in regards to FIG. 1 and FIG. 2.

At step 320, DAC hardware converts the optimally formatted digital data, which has since been calibrated at step 310, back to analog data. Next, in one possible embodiment, analog data may be passed to voltage divider box to adjust the voltages associated with the analog data such as by a factor of 1:1000. These steps allow the receiving ECG machine to readily distinguish between the different electrode leads, given the voltages produced by the human body are small and nearly indiscernible without amplification. Finally at step 340, the receiving ECG machine reconverts analog data to digital data, after which the receiving ECG machine's diagnostic algorithm analyzes digital data for a clinical diagnosis.

FIG. 4 depicts one possible general hardware configuration for use in accord with one possible embodiment of the present invention. The invention is not limited to this particular hardware and may comprise different hardware configurations. In this configuration, Pandaboard ES 404 is responsible for receiving the optimally formatted digital information into the system, whether that is streaming data, stored data, or data otherwise accessible by Pandaboard ES 404. Next, breakout circuits interface the voltage levels of the received digital data to properly interface with digital to analog converter 402, because the voltage levels should be amplified to return to analog signals. Right arm electrode 406 is grounded to right leg electrode 408 at the voltage divider box through resistor 412, which provides the receiving ECG machine the substantially same impedance as would be provided for electrodes positioned on the living creature.

While the present signals are not perfect reproductions, future technological developments, both in DAC and in ADC technologies, will likely further improve the quality of reproduction. In relation to this, it should be noted that the Cardiax and CorScience ADCs used in the aforementioned validation studies utilize, like the majority of other commercially available ECG devices, known non-optimal methods of ADC sampling that implement "time interleaving". Importantly, such methods alone, whether they implement "round robin", i.e. Cardiax, or "pseudo-simultaneous", i.e.

CorScience, sampling, these devices may introduce subtle distortions into any digitized data, and then necessarily into the re-digitized data. Newer ECG devices introduced into the market, including an upgraded Cardiax device, are able to employ a more truly simultaneous method of ADC sampling by faster processor chips; for instance, Texas Instruments' ADS 1298. Therefore, data collected on ECG devices employing such newer chips may, with even greater fidelity, be re-convertible back to the original analog and then again to an even higher quality state of re-digitization when used in accord with the present invention described herein.

As discussed hereinbefore, future systems like the one described herein may be able to more efficiently and accurately simulate the original analog data as technology improves, particularly when combined with ECG recorders that employ true simultaneous sampling and higher sampling rates.

Detailed descriptions of the preferred embodiment are provided herein. It is to be understood, however, that the present invention may be embodied in various forms. Therefore, specific details disclosed herein are not to be interpreted as limiting, but rather as a basis for the claims and as a representative basis for teaching one skilled in the art to employ the present invention in virtually any appropriately detailed system, structure or manner.

The foregoing description of the preferred embodiments of the invention has been presented for purposes of illustration and description only. It is not intended to be exhaustive, nor to limit the invention to the precise form disclosed; and obviously many modifications and variations are possible in light of the above teaching. Such modifications and variations that may be apparent to a person skilled in the art are intended to be included within the scope of this invention as defined by the accompanying claims.

What is claimed is:

1. A method of digital to analog transformation for reconstruction of a first set of analog signals from digital information representative of said first set of analog signals wherein said digital information is generated by a first electrocardiogram (ECG) machine and wherein said reconstruction results in a second set of analog signals capable of use as an input into at least a second ECG machine, comprising the steps of:
    receiving said digital information representative of said first set of analog signals and consisting of eight independent signals, wherein each independent signal represents at least one of a plurality of electrical potentials (i) between at least one pair of a plurality of electrodes placed on a living creature or (ii) between at least one individual electrode from said plurality of electrodes placed on said living creature and a predetermined reference;
    utilizing a digital-to-analog (DAC) device to produce said second set of analog signals comprising nine analog outputs from said digital information wherein a first analog output of said nine analog outputs is designated as a common reference;
    utilizing said DAC device to impose a predetermined voltage on a second analog output of said nine analog outputs with respect to said common reference; and
    utilizing said second set of analog signals as said input into said at least said second ECG machine,
wherein said second set of analog signals represents a clinically sufficient approximation of said first set of analog signals.

2. The method of claim 1, wherein said step of receiving said digital information is further comprised of receiving said digital information in a predetermined format.

3. The method of claim 2, further comprising the step of:
    utilizing a processor to convert said digital information from said predetermined format to a predetermined optimal format, wherein said predetermined optimal format is comprised of said first analog output designated as said common reference and wherein said first analog output corresponds to a first electrode of said plurality of electrodes.

4. The method of claim 3, wherein said first electrode of said plurality of electrodes is an electrode placed on a limb of said living creature.

5. The method of claim 4, wherein said plurality of electrodes comprises a plurality of limb electrodes and a plurality of precordial electrodes configured to produce a first ECG recording.

6. The method of claim 5, wherein said plurality of limb electrodes comprises a right arm electrode, a left arm electrode, a right leg electrode, and a left leg electrode.

7. The method of claim 4, wherein said second analog output corresponds to a second electrode of said plurality of electrodes comprising a second limb of said living creature.

8. The method of claim 1, wherein said step of utilizing said DAC device to impose said predetermined voltage comprises imposing a zero voltage on said second analog output.

9. The method of claim 8, wherein said imposing said zero voltage on said second analog output comprises electrically connecting said second analog output to said common reference.

10. The method of claim 9, wherein said electrically connecting said second analog output to said common reference comprises connecting said second analog output to said common reference through a resistor utilized for impedance matching.

11. The method of claim 1, wherein said plurality of electrodes comprises a plurality of limb electrodes and a plurality of precordial electrodes configured to produce a first ECG recording by said first ECG machine.

12. The method of claim 11, further comprising the steps of:
    utilizing said first set of analog signals and said first ECG machine to produce said first ECG recording and a first set of at least one automated diagnostic statement;
    utilizing said second set of analog signals and said second ECG machine to produce a second ECG recording and a second set of at least one automated diagnostic statement;
    comparing said first set of at least one automated diagnostic statement to said second set of at least one automated diagnostic statement; and
    identifying differences, if any, between said first set of at least one automated diagnostic statement and said second set of at least one automated diagnostic statement.

13. The method of claim 11, wherein said at least said second ECG machine is comprised of a plurality of ECG machines and further comprising the steps of:
    utilizing said first set of analog signals and said first ECG machine to produce said first ECG recording and a first set of at least one automated diagnostic statement;
    utilizing said second set of analog signals and said plurality of ECG machines to produce a plurality of ECG recordings and a plurality of sets of at least one diagnostic statement;

comparing said first set of at least one diagnostic statement and said plurality of sets of at least one diagnostic statement to each other; and identifying differences, if any, among said first set of at least one diagnostic statement and said plurality of sets of at least one diagnostic statement.

* * * * *